United States Patent [19]

Dorer et al.

[11] Patent Number: 4,945,902
[45] Date of Patent: Aug. 7, 1990

[54] PROGRESSIVE STATIC FLEXION DEVICE FOR PHALANGES

[75] Inventors: Robert E. Dorer, Thousand Oaks; Lawrence Belden, Pacific Palisades, both of Calif.

[73] Assignee: Bissell Health Care Corporation, Grand Rapids, Mich.

[21] Appl. No.: 284,668

[22] Filed: Dec. 15, 1988

[51] Int. Cl.$^5$ .................................................. A61F 5/10
[52] U.S. Cl. ...................................... 128/87 A; 128/26
[58] Field of Search ..................... 128/26, 25 R, 25 B, 128/77, 69, 84 R, 84 C, 68, 87 R, 87 A; 272/67

[56] References Cited

U.S. PATENT DOCUMENTS

| | | | |
|---|---|---|---|
| 3,457,912 | 7/1969 | Clark et al. | 128/26 |
| 3,714,940 | 2/1973 | Palmer | 128/77 |
| 3,756,222 | 9/1973 | Ketchum | 128/26 |
| 4,441,489 | 4/1984 | Evans et al. | 128/77 |
| 4,576,148 | 3/1986 | Koerner et al. | 128/26 |
| 4,602,620 | 7/1986 | Marx | 128/77 |
| 4,604,997 | 8/1986 | DeBastiani et al. | 08/86 |
| 4,607,625 | 8/1986 | Schenck | 128/26 |
| 4,644,938 | 2/1987 | Yates et al. | 02/87 |
| 4,679,548 | 7/1987 | Pecheux | 07/87 |
| 4,716,889 | 1/1988 | Saringer | 128/25 R |
| 4,719,906 | 1/1988 | DeProspero | 128/87 |
| 4,724,827 | 2/1988 | Schenck | 128/26 |
| 4,765,320 | 8/1988 | Lindemann et al. | 128/87 A |

FOREIGN PATENT DOCUMENTS 293622 8/1915 Fed. Rep. of Germany ... 128/87 A

OTHER PUBLICATIONS

Publication entitled, "Flexible Implant Resection Arthroplasty in the Hand and Extremities", by Alfred Swanson, MD, 1983, pp. 174-181.

Primary Examiner—Richard J. Apley
Assistant Examiner—H. N. Flaxman
Attorney, Agent, or Firm—Price, Heneveld, Cooper, DeWitt & Litton

[57] ABSTRACT

A device for progressively applying a flexion force to a phalange includes a fraction-force producing portion for applying long-axis traction to the finger and a flexion-force producing portion, that is infinitely adjustable within a wide range of lengths, for applying a flexion force directly to the proximal phalanx generally perpendicular the long-axis of the bone. The flexion force is adjustable independently of the traction force. Embodiments are disclosed for providing progressive flexion to one finger, two adjacent fingers, or the thumb.

29 Claims, 6 Drawing Sheets

PROGRESSIVE STATIC FLEXION DEVICE FOR PHALANGES

BACKGROUND OF THE INVENTION

This invention relates to a device for applying flexion to a phalanx and in particular to a passive flexion device which may additionally provide dynamic long-axis traction to the respective joint.

Severe limitations in range-of-motion flexion of the metacarpophalangeal joint can occur with dorsal wounds, skin grafts, skin burns, extensor tendon injuries, fracture of the metacarpal or proximal phalanges and complications from pain. Restoring passive flexion once range-of-motion limitation is established is very difficult. The metacarpophalangeal joint has a unique cog-shape and is combined with a complicated system of ligament and periarticular support which permits the joint to flex and to extend with excellent lateral stability. This very structure, however, is responsible for the difficulty in restoring passive flexion, especially when the collateral ligaments have become seriously shortened from positioning of the joint without flexion for a prolonged period.

The present invention is directed to restoring passive range-of-motion in the metacarpophalangeal joint following limitations upon such flexion.

SUMMARY OF THE INVENTION

The present invention facilitates the application of dynamic long-axis traction to the finger, in order to stretch the shortened colateral ligaments, to restore the joint space between the base of the proximal phalanx and the metacarpal head and to permit the proximal phalanx to flex over the widest part of the cog-shape of the head of the metacarpus. At the same time, gradually progressive, yet static, flexion force is applied to the proximal phalanx independently of the dynamic long-axis traction force. These and other related objects, advantages and features of this invention will become apparent upon review of the following specification in conjunction with the drawings.

BRIEF DESCRIPTION OF THE DRAWINGS

FIG. 6b is a perspective view of a portion of the base of the device illustrated in FIG. 6a;

FIG. 7b is the same view as that in FIG. 7a with a portion of the wrist splint removed to reveal additional structure of the device in FIG. 7a.

DESCRIPTION OF THE PREFERRED EMBODIMENT

Figure 1A:
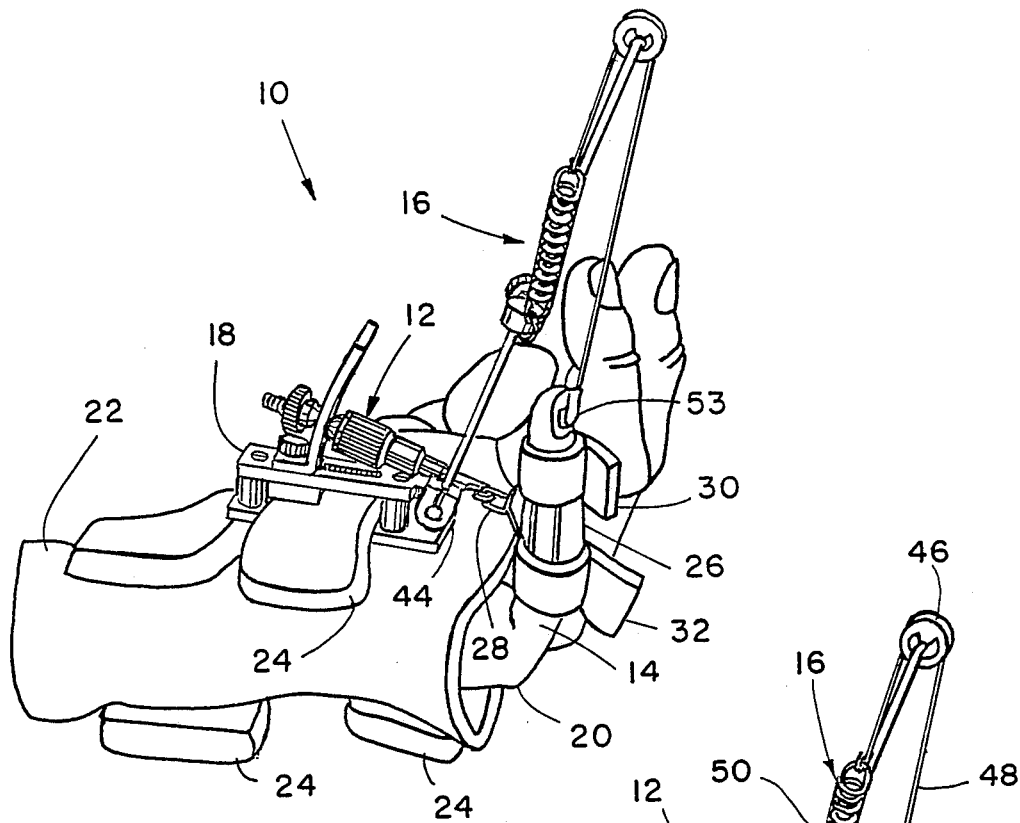
FIG. 1a is a perspective view of a progressive static flexion device according to the invention in use on a hand providing long-axis traction and flexion to a phalanx.
Figure 1B:
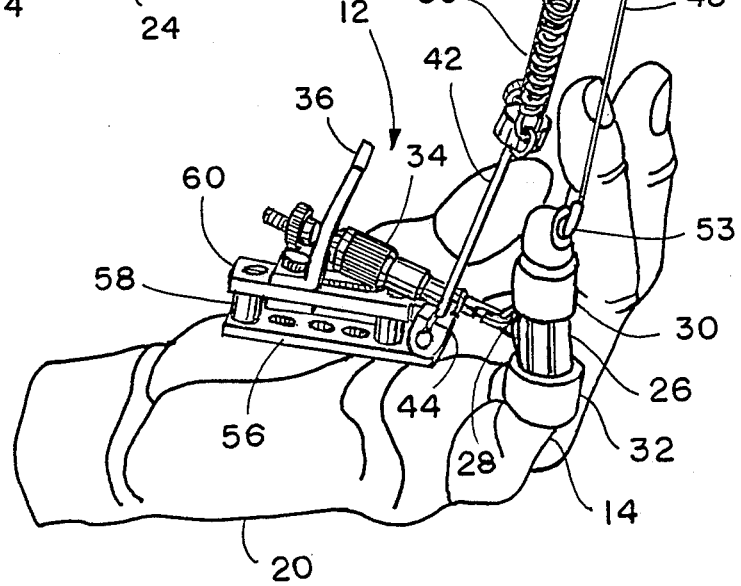
FIG. 1b is the same view as FIG. 1a with the wrist splint removed to reveal additional structure of the flexion traction device.

Referring now specifically to the drawings, and the illustrative embodiments depicted therein, a progressive static flexion device for phalanges, generally shown at 10, includes flexion means 12 for providing passive flexion to a finger 14 and a traction means 16 for applying long-axis traction to finger 14. Flexion means 12 and traction means 16 are commonly mounted on a base 18 which is configured to conform substantially to the surface of the palm of hand 20. Flexion device 10 is mounted to the hand 20 by a hand or wrist splint 22 which per se forms no part of the invention. In the illustrated embodiment, splint 22 is molded to the configuration of the patient's wrist and hand from low-temperature thermoformable plastic and is stabilized by fastening straps 24 which attach to the outer surface of splint 22 by fasteners (not shown). The purpose of splint 22 is to provide thermal isolation between the progressive static traction device 10 and the skin of the patient to avoid discomfort that would result from the metallic structure of the device 10 coming in contact with the skin. Additionally, splint 22 provides stability to device 10 to distribute the forces transmitted to base 18 over a larger portion of hand 20. Straps 24 serve to retain flexion device 10 firmly against splint 22 and therefore in an appropriate orientation adjacent the palm of hand 20, in a manner that will be explained in detail below.

Flexion device 10 is used in conjunction with a conventional finger splint 26 applied to the proximal phalanx and further including a loop 28 extending rearwardly from upper and lower portions 30 and 32 of splint 26. Flexion means 12 includes a rod 34 which extends generally parallel the palm between a support member 36, extending from base 18, and loop 28, which is engaged by a hook 38 at the end of rod 34 opposite support member 36. In this manner, rod 34 is capable of transmitting a flexion force on the proximal phalanx of finger 14 from support member 36, which is firmly supported by the hand through base 18 and splint 26.

Figures 2, 8:
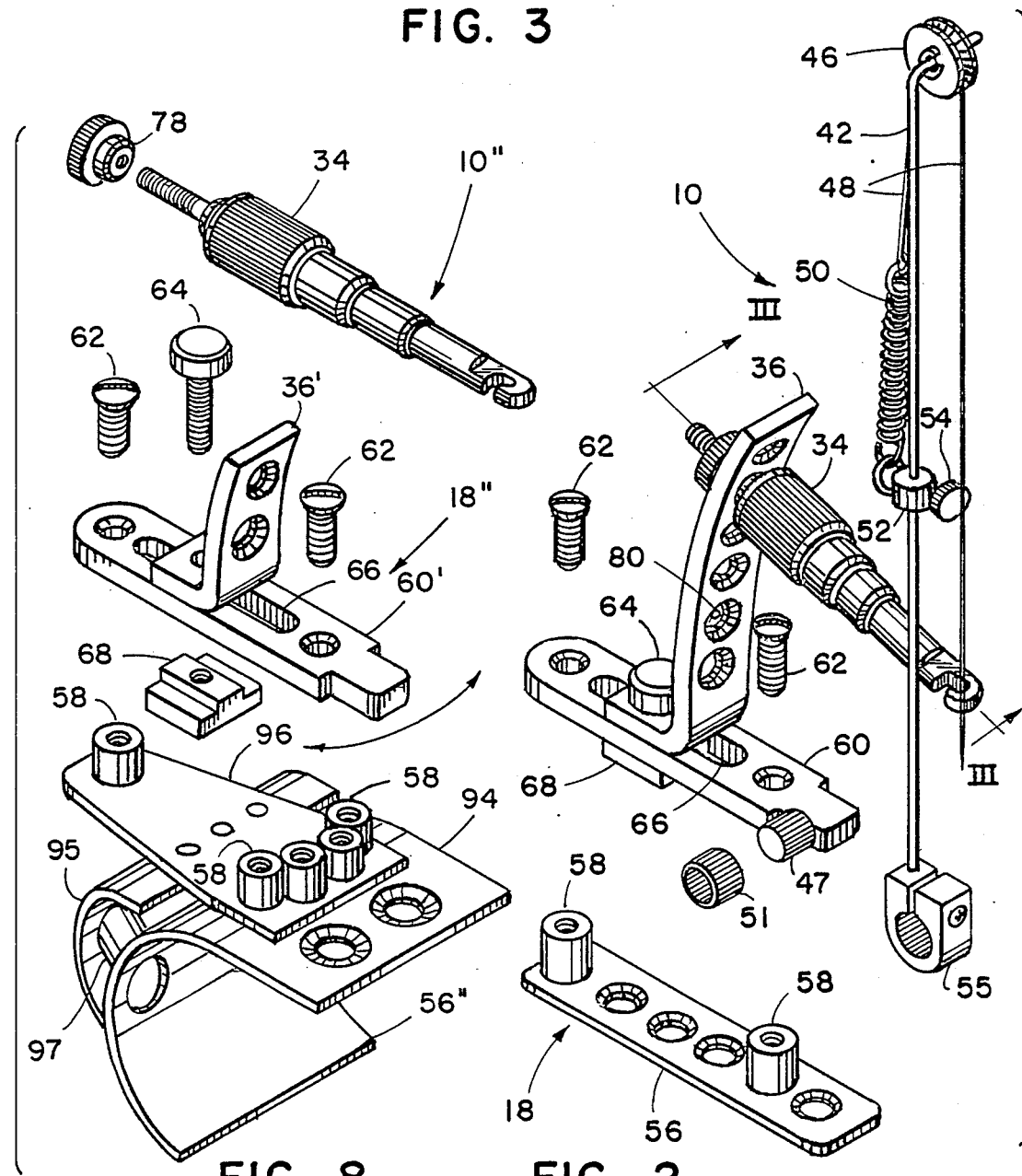
FIG. 2 is an exploded perspective view of the flexion device illustrated in FIGS. 1a and 1b.
FIG. 8 is an exploded perspective view of the device illustrated in FIGS. 7a and 7b.

Progressive flexion device 10, in the illustrated embodiment, additionally includes traction means 16 which has a shaft 42 coupled at one end to base 18 by pivotal coupling 44 and a pulley 46 rotatably mounted at an end opposite coupling 44. A line 48 is attached by attachment means 49 to the fingernail of finger 14 and extends over pulley 46. A spring 50 is attached to the opposite end of line 48 and provides tensioning means for keeping line 48 under tension. The free end of spring 50 is connected to shaft 42 by adjustable attachment means 52, which is capable of selective positioning along shaft 42 and retention at a desired position by a clamping screw 54. The attachment means for attachment of line 48 to the fingernail of finger 14, includes a finger hook 53 attached to the fingernail by an adhesive such as SUPERGLUE ™ and is readily removable by a solvent such as acetone. In the illustrated embodiment, finger hook 53 is a number 2 dress hook used in the garment industry. Alternatively, a fingernail suture could be used. Pivotal coupling 44 includes a clamp 55 rotatably mounted to a stud 47 attached to a portion of base 18 (FIG. 2). A bushing 51 is rotatably retained on stud 47 and is engaged by clamp 45 to pivotally attach traction means 16 to base 18.

Base 18 includes a first, lower plate member 56 which conforms to the relatively flat surface of the palm of hand 20 and includes a pair of threaded spacers 58 extending upwardly therefrom. A second, upper plate 60 is attached to spacers 58 by fasteners 62 to form a rigid base assembly Plate 60 is, accordingly, spaced apart from plate 56 by the length of spacers 58 to provide a passage through which strap 24 of splint 22 may be passed in order to attach flexion device 10 firmly to splint 22. Support member 36 is attached to upper plate 60 by a fastener 64 extending through the support member and an elongated opening 66 in plate 60. Fastener 64 is threadably received by a backing plate 68 positioned on the opposite side of plate 60. Because opening 66 is elongated, support member 36 may be selectively positioned longitudinally along plate 60 by loosening fastener 64.

Figure 3:
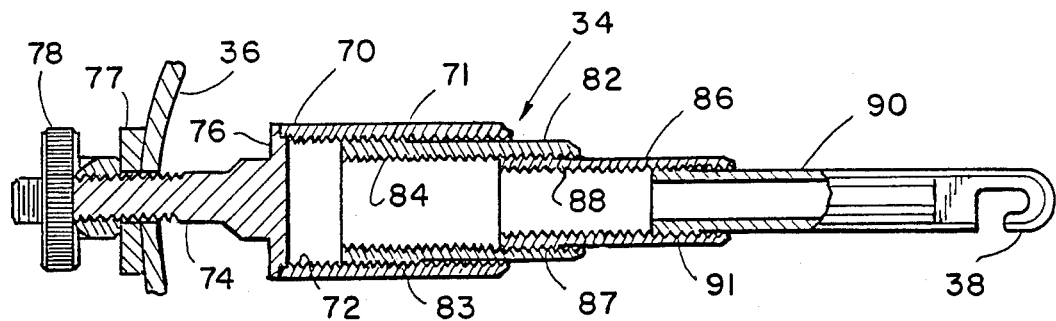
FIG. 3 is a sectional view taken along the lines III—III in FIG. 2.
Figure 4:
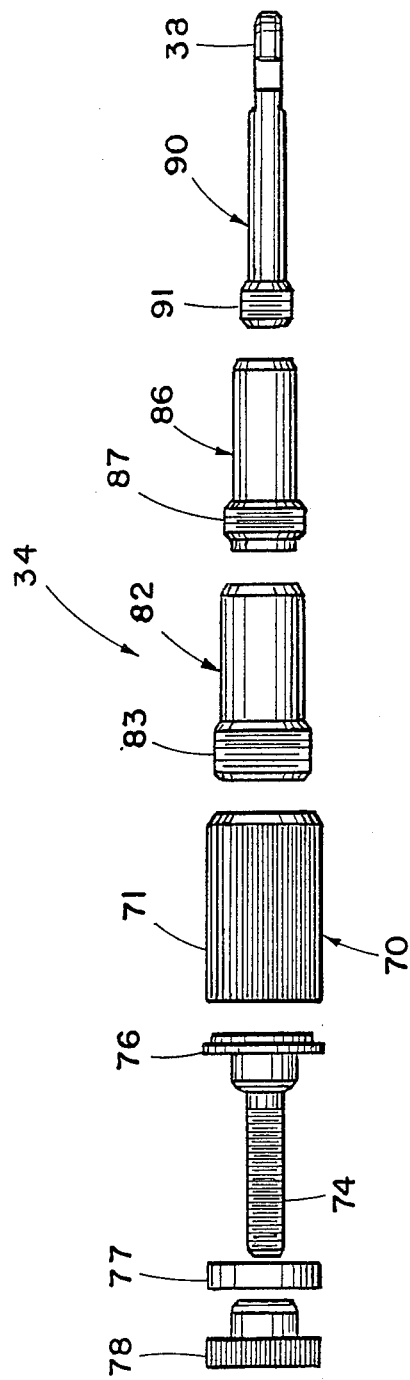
FIG. 4 is an enlarged, exploded side view of the components of the rod illustrated in FIG. 3.

Adjustable rod 34 of flexion means 12 includes a first sleeve 70 having a knurled outer surface 71 and an internally threaded surface 72 (FIGS. 3 and 4). A mounting stud 74 is attached by an integral disk 76 attached to an end of sleeve 70 as by welding, or the like. Stud 74 is threaded to receive a nut 77 and locking nut 78 thereon. Stud 74 is adapted to pass through one of a plurality of openings 80 positioned along support member 36 at various distances from base 18. With stud 74 in one opening 80, nut 77 is threaded on the stud and lock nut 78 threaded against nut 77 to prevent relative rotation of nut 77 on stud 74. In this manner, sleeve 70 is rotatably mounted by support member 36.

Rod 34 further includes a second sleeve 82 having an internally threaded surface 84 and an externally threaded surface 83 adapted to threadably engage surface 72 of first sleeve 70. With threaded surfaces 83 and 72 engaged, second sleeve 82 is telescopingly received within, and longitudinally adjustable with respect to, first sleeve 70 by relative rotation between the sleeves. Rod 34 additionally includes a third sleeve 86 having an internally threaded surface 88 and an externally threaded surface 87 adapted to threadably engage threaded surface 84 of second sleeve 82. With threaded surfaces 84 and 87 engaged, third sleeve 86 is telescopingly received within, and longitudinally adjustable with respect to, second sleeve 82 by relative rotation between sleeves 82 and 86. A fourth sleeve 90 includes a hook 38 at one end thereof and an external threaded surface 91 adapted to threadably engage threaded surface 88 of sleeve 86. With threaded surfaces 88 and 91 engaged, fourth sleeve 90 is telescopingly received within, and longitudinally adjustable with respect to, third sleeve 86 by relative rotation between sleeves 86 and 90.

The structure described above provides infinite, or nonincremental, adjustment of the length of rod 34 between a fully extended position and a fully retracted position. The rotation of first sleeve 70, with respect to support member 36, will cause second sleeve 82 to extend or retract with respect to first sleeve 70. If first sleeve 70 is rotated sufficiently to cause second sleeve 82 to be fully received within sleeve 70, second sleeve 82 will bottom-out and will rotate with sleeve 70. This will cause relative rotation between second sleeve 82 and third sleeve 86 which will cause third sleeve 86 to be retracted within second sleeve 82 until third sleeve 86 bottoms-out within second sleeve 82. Further rotation of sleeve 70 will cause the first, second and third sleeves to rotate together causing retraction of fourth sleeve 90 until fourth sleeve 90 is bottomed-out within third sleeve 86. Thus, it is seen that rod 34 is provided with an infinite degree of adjustability over a wide range of lengths.

Figure 5A:
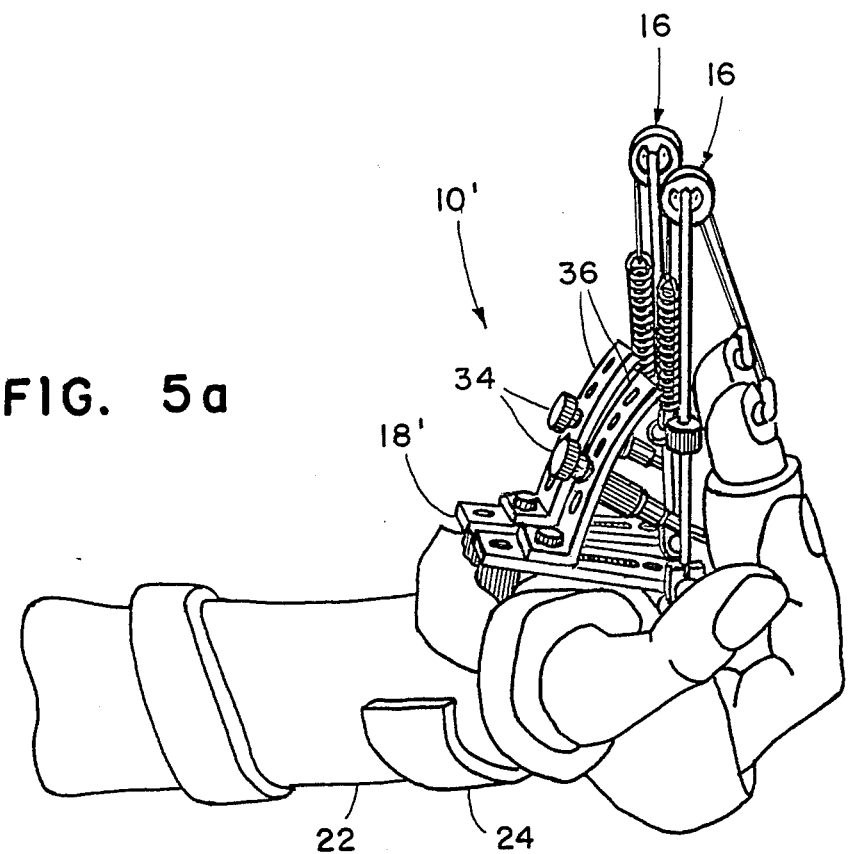
FIG. 5a is a perspective view of another embodiment of the invention illustrated in use on a hand.
Figure 5B:
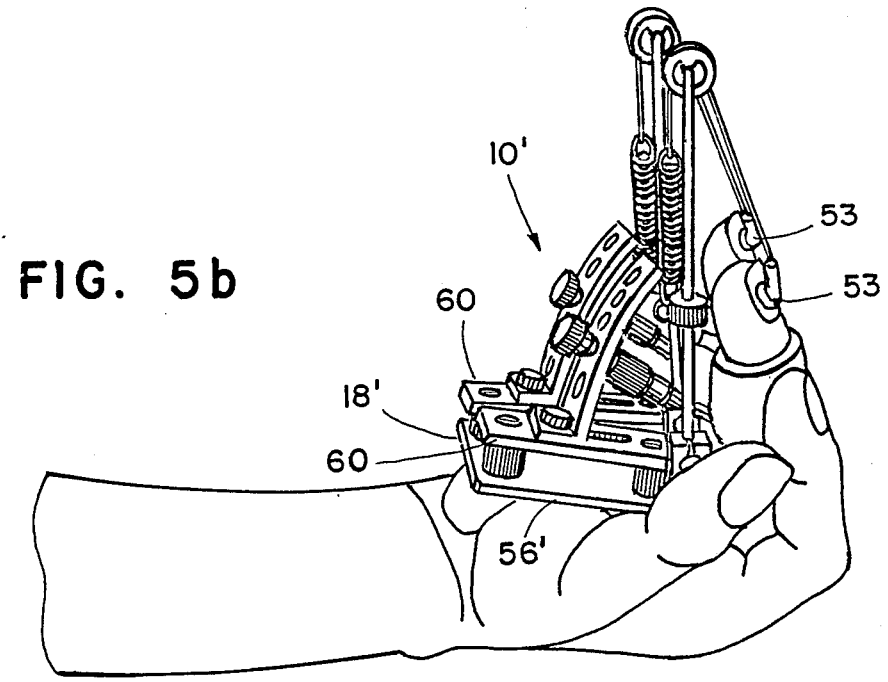
FIG. 5b is the same view as FIG. 5a with the wrist splint removed to reveal additional structure of the flexion device.
Figure 6A:
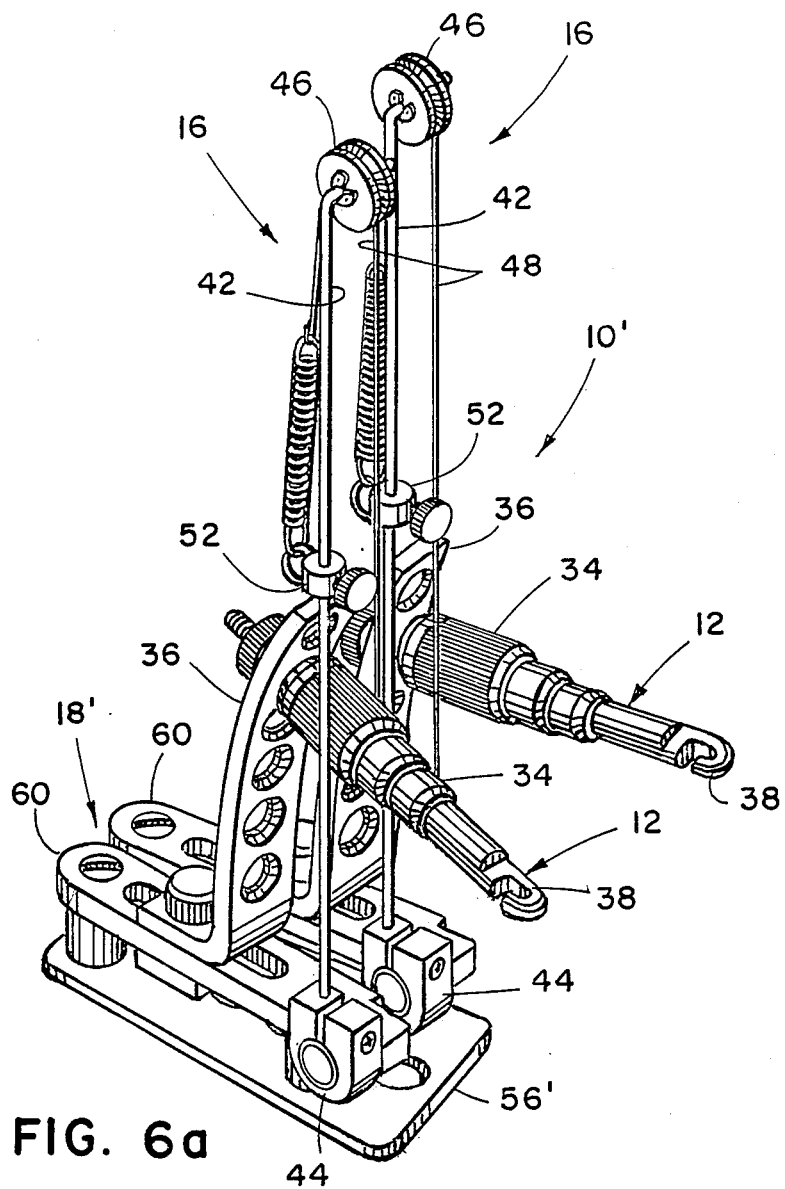
FIG. 6a is an enlarged perspective view of the flexion device illustrated in FIGS. 5a and 5b.
Figure 6B:
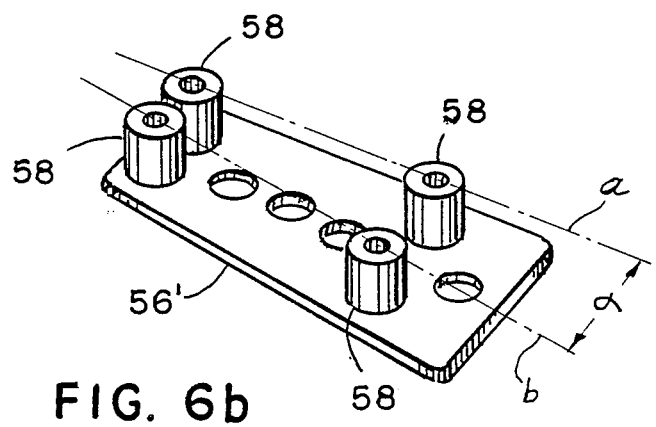

In an embodiment of the invention illustrated in FIGS. 5a through 6b, a progressive static flexion device 10' is provided for applying progressive passive flexion and long-axis traction to two adjacent phalanges. Flexion device 10' is, in essence, a combination of two flexion devices 10 having a common base 18'. Base 18' includes conforming plate 56' having two pair of threaded spacers 58 (FIG. 6b). Centerlines "a" passing through two longitudinally separated spacers 58, and "b" passing through the other pair of spacers 58, are angularly related by an angle a. As illustrated in FIG. 6a, with one plate 60 attached to each set of spacers 58, the pair of flexion means 12 have essentially the same offset angle between them. The purpose of this offset is to properly align the flexion means with the flexion axis of the respective phalanges. As illustrated in FIGS. 5a and 5b, lower plate 56' of base 18' is configured to substantially conform to the palm of the hand and is attached to wrist splint 22 in the same manner as in the previously-described embodiment. With flexion device 10', each flexion means 12 and traction means 16 is independently adjustable to provide progressive static flexion and long-axis traction as appropriate for the respective phalanx.

Figure 7A:
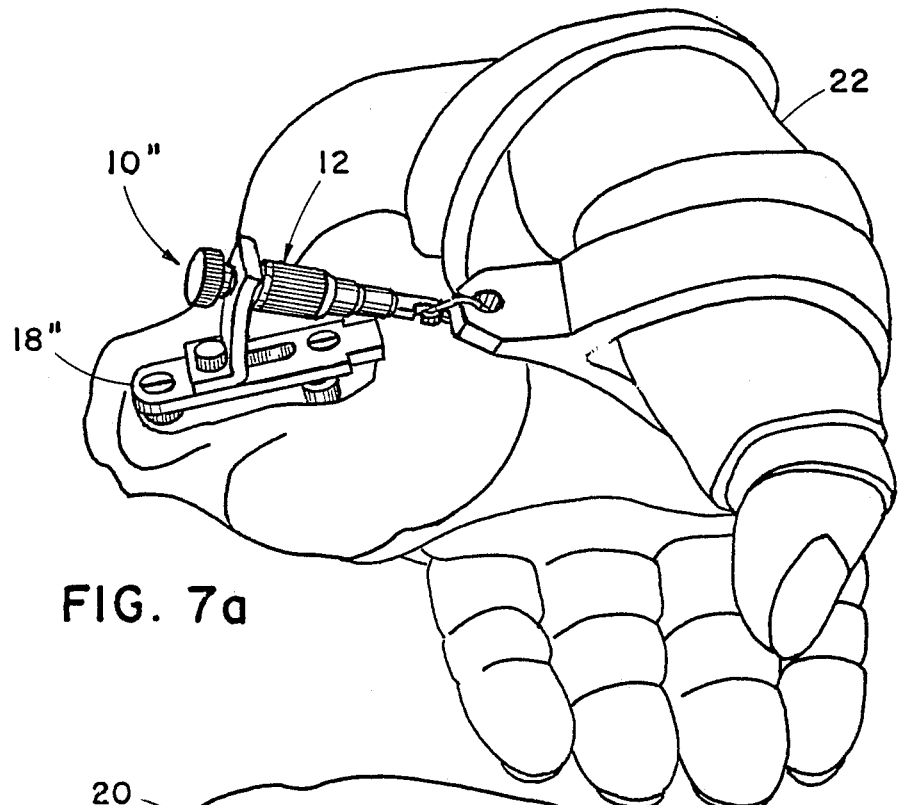
FIG. 7a is a perspective view of yet another embodiment of the invention illustrated in use applying passive flexion to the thumb of a patient's hand.
Figure 7B:
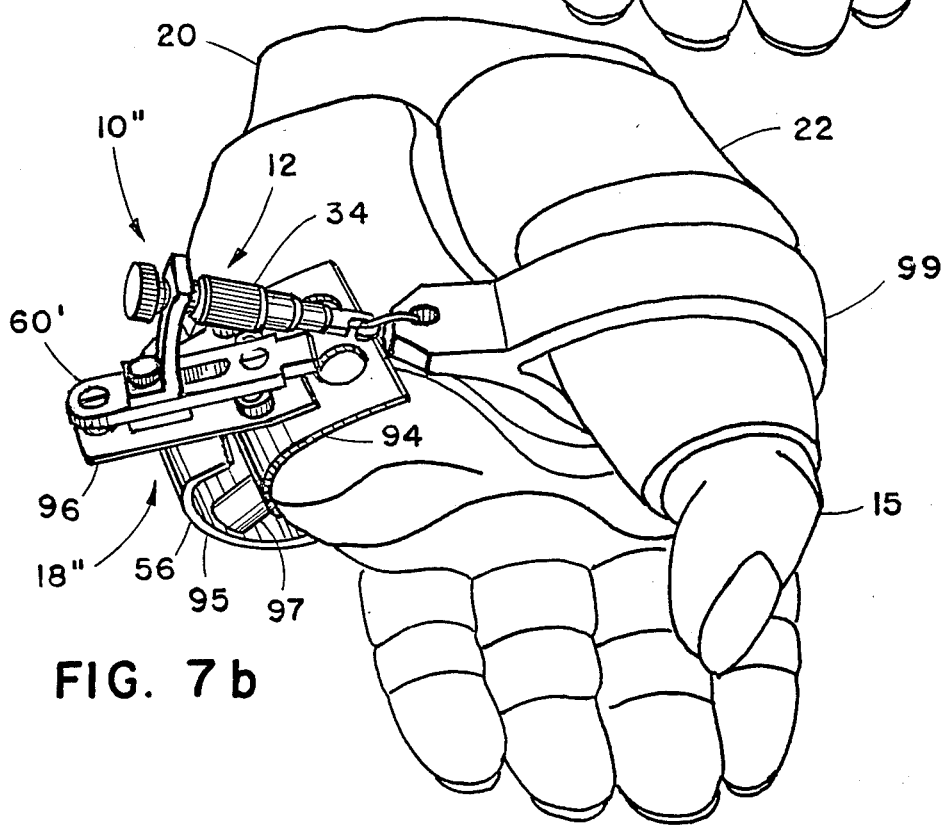

The invention may also be utilized to provide passive flexion to a phalanx without long-axis traction. In FIGS. 7a through 8, a flexion device 10'' is illustrated applying passive flexion to the thumb 15 of hand 20. Flexion device 10'' includes a base 1B'' having a plate 56'' configured to wrap around the interior surface of the hand opposite the thumb and conform to the adjacent portion of the palm of the hand. Plate 56'' has three rigidly interconnected portions. It includes an inner curved portion 94, configured to the portion of the hand opposite the thumb, an outer curved portion 95 and an upper portion 96. Portions 94 and 95 are interconnected through spacers 97. Upper portion 96 is attached at one end to inner curved portion 94 and at an opposite end to outer curved portion 95. In this manner, base 18'' is capable of suitable attachment to cast 22 by straps extending between inner and outer portions 94 and 95 and between upper portion 96 and plate 60'. Upper portion 96 includes a single threaded spacer 58 at one end and a plurality of threaded spacers 58 arranged in an arc at an opposite end. The purpose of the plurality of spacers 58 at one end is to allow adjustment of the angle between plate 60' and base 18'' in order to adapt flexion device 10'' to the size of the patient's hand, to provide true flexion force to the thumb. Flexion device 10'' is illustrated applying a flexion force to thumb 15 through a sling 99 extending over the proximal phalanx thereof.

In operation, the progressive static flexion device is assembled to the patient's hand and attachment member 52 is appropriately positioned along shaft 42 to apply the desired traction force along the long-axis of the finger. Sleeve 70 is rotated to progressively apply a flexion force to the proximal phalanx as tolerated by the patient. After a "rest", or quiescent period, additional flexion may be provided by further rotation of sleeve 70. Rotation of sleeve 70 in the opposite direction relieves the flexion force, if necessary, for sleeping or to remove the device. As the amount of flexion is modified, shaft 42 will pivot about coupling 44 to maintain the traction line-of-pull in the long-axis of the finger. Traction means 16 may be supplied in two different lengths: one for flexion of 45-90 and a longer length for flexion of 0-45°.

The present invention is capable of providing long-axis traction to the phalanges to enhance flexion of the metacarpophalangeal joint while providing passive flexion which is infinitely adjustable within a wide range. Because the flexion force is applied directly to the proximal phalanx and is applied perpendicular to the long axis of the phalanx, a true flexion force is provided which is capable of very fine adjustment of the amount of flexion provided. It is seen that the invention provides for passive flexion which is applied independently of the long-axis traction of the phalange. The present invention, thus, provides a much greater control over the therapy than previous devices. Because correct "line of pull" is provided for both long-axis traction and flexion, the comfort of flexing is enhanced. The patient develops 24-hour tolerance of the device very quickly, which additionally expedites the therapy of the patient. Because the flexion means is infinitely adjustable in length, the patient is allowed to stop at any point of flexion and "rest" until he/she is ready to progress further In the illustrated embodiment, the components are made of surgical stainless steel to be autoclavable and reusable. Changes and modifications in the specifically described embodiments can be carried out without departing from the principles of the invention which is intended to be limited only by the scope of the appended claims, as interpreted according to the principles of patent law including the doctrine of equivalents.

The embodiments of the invention in which an exclusive property or privilege is claimed are defined as follows.

1. A passive flexion system for applying passive flexion to multiple phalanges of the same hand, said system comprising:
    a plurality of devices operative independently of each other to apply traction and flexion forces to a plurality of phalanges, each one of said devices including
    traction means for applying long-axis traction to the respective phalange;
    flexion means for applying flexion force to the respective phalange;
    said flexion means adapted to apply said flexion force directly to the respective proximal phalanx and generally perpendicular to said longaxis traction whereby the flexion force may be controlled independent of the traction force, said system further including a palmar base, said plurality of devices being attached to said base, said base is adapted for connection to the hand adjacent the palm.

2. A passive flexion system for applying passive flexion to multiple phalanges of the same hand, said system comprising:
    a plurality of devices operative independently of each other to apply traction and flexion forces to a plurality of phalanges, each one of said devices including
    traction means for applying long-axis traction to the respective phalange;
    flexion means for applying flexion force to the respective phalange;
    said flexion means adapted to apply said flexion force directly to the respective proximal phalanx whereby the flexion force may be controlled independent of the traction force; said system further including a base, said plurality of devices being attached to said base, said base being adapted for connection to the hand adjacent the palm, and
    each said flexion means including a rod positioned substantially parallel the palm, said rod having a first and attached to a support member associated with the respective one of said devices and extending from said base, said rod having an opposite end having attachment means for attachment of said rod to the proximal phalanx.

3. The system in claim 2 in which said attachment means includes a hook on said opposite end and a splint around the phalange and having a loop engaged by said hook.

4. The system in claim 2 in which said rod includes adjusting means for manually varying the distance between said ends, whereby said flexion means is capable of flexing the proximal phalange to various selectable positions.

5. The system in claim 4 in which said adjusting means is infinitely adjustable within predefined limits.

6. The system in claim 1 in which each said traction means includes an elongated member pivotally attached at one end to said base.

7. The system in claim 6 in which said elongated member includes a shaft having a pulley positioned at an end opposite said one end and in which said traction means further includes a line extending over said pulley and tensioning means for attaching one end of said line selectively to a position along said shaft.

8. A passive flexion device for a finger of a hand comprising:
    a base configured to substantially conform to the palm of the hand;
    traction means extending from said base for applying traction along the long-axis of the finger;
    flexion means extending from said base for applying a force substantially perpendicular to the long-axis of the finger and generally parallel to the palm and base; and
    said flexion means operative independent of said traction means, whereby the flexion of the finger may be established solely by said flexion means, said flexion means further including adjustment means for manually adjusting the flexion of the finger and wherein said adjustment means is continuously adjustable.

9. A passive flexion device for a finger of a hand comprising:
    a base configured to substantially conform to the palm of the hand;
    traction means extending from said base for applying traction along the long-axis of the finger;
    flexion means extending from said base for applying a force substantially perpendicular to the long-axis of the finger;
    said flexion means operative independent of said traction means, whereby the flexion of the finger may be established solely by said flexion means; and
    adjustment means associated with said flexion means for manually adjusting the flexion of the finger, said adjustment means being continuously adjustable, and wherein
said adjustment means includes a support member and a rod assembly extending between said support member and the finger, said rod having an adjustable length.

10. A passive flexion device for a finger comprising:
traction means for applying traction along the long-axis of the finger;
flexion means for applying a force substantially perpendicular to the long-axis of the finger;
adjustment means associated with said flexion means for adjusting the flexion of the finger, said adjustment means being continuously adjustable and including a support member and a rod assembly extending between said support member and the finger, said rod having an adjustable length and including a first sleeve member attached to said support member and a second sleeve member telescopingly threadably joined with said first sleeve member, whereby rotation of said first sleeve member will cause said members to telescope;
said flexion means operative independent of said traction means, whereby the flexion of the finger may be established solely by said flexion means.

11. The device in claim 10 in which said rod assembly further includes a third sleeve member telescopingly threadably joined with said second sleeve member, whereby rotation of said first sleeve will cause said second and third sleeve members to telescope when said first and second sleeve members are fully telescoped and rotating together.

12. The device in claim 11 in which said rod assembly further includes a fourth sleeve member telescopingly threadably joined with said third sleeve member and including a hook portion on an end opposite the portion joined with said third sleeve member, whereby rotation of said first sleeve will cause said third and fourth sleeve members to telescope when said second and third sleeve members are fully telescoped and rotating together.

13. The device in claim 9 in which said support member extends substantially perpendicularly from said base member and said rod assembly extends substantially perpendicularly from said support member.

14. A passive flexion device for a finger comprising:
traction means for applying traction along the long-axis of the finger:
flexion means for applying a force substantially perpendicular to the long-axis of the finger;
adjustment means associated with said flexion means for adjusting the flexion of the finger, said adjustment means being continuously adjustable and including a support member and a rod assembly extending between said support member and the finger, said rod having an adjustable length, said flexion means including a base member adapted for attachment adjacent the palm of the hand, said support member extending substantially perpendicularly from said base member, said support member including means defining a plurality of openings spaced various distances from said base member, said rod including means for selectively engaging one of said openings;
said flexion means operative independent of said traction means, whereby the flexion of the finger may be established solely by said flexion means.

15. The device in claim 8 including pivot means for pivotally attaching said traction means to said base.

16. The device in claim 15 in which said traction means includes an elongated shaft extending from said base, and pulling means associated with an end of said shaft opposite said pivot means for applying a force parallel said shaft and away from said base.

17. The device in claim 16 in which said pulling means includes a pulley on said end of said shaft, a line extending over said pulley and tensioning means for attaching one end of said line selectively to a position along said shaft.

18. The device in claim 13 in which said line includes a tension spring portion.

19. A passive flexion device adapted to be attached adjacent the palm of a hand by a strap extending around the hand for applying passive flexion to a finger on the hand, said device comprising:
a base configured to substantially conform to the palm of the hand, said base including means defining a lateral passage through said base configured to receive a strap through said passage;
a support member extending generally perpendicular from said base and attached thereto attaching means, said support member defining a plurality of openings spaced various distances from said base; and
a rod assembly having a first end attached to said support member at one of said openings and a second end adapted for attachment to the proximal phalanx;
said rod extending from said support member generally parallel to said base and in a manner to produce a flexion force on the proximal phalange perpendicular the long-axis thereof;
said rod assembly continuously manually adjustable in length, whereby a continuously adjustable static flexion force may be applied to the phalange/metacarpal joint.

20. The device in claim 19 in which said base includes a bottom plate conforming to the palm of the hand and a second upper plate spaced from said first plate, said passage being defined between said plates.

21. A passive flexion device adapted to be attached to the palm of a hand by a strap extending around the hand for applying passive flexion to a finger on the hand, said device comprising:
a base configured to substantially conform to the palm of the hand, said base including means defining a lateral passage through said base configured to receive a strap through said passage, said base including a bottom plate conforming to the palm of the hand and a second upper plate spaced from said first plate, said passage being defined between said plates, said second plate includes edge means defining an elongated opening therein;
a support member extending from said base and attached thereto by attaching means, said attaching means being adjustable in said elongated opening to provide adjustment between said support member and said base;
a rod assembly having a first end attached to said support member and a second end adapted for attachment to the proximal phalanx;
said rod extending from said support member in a manner to produce a flexion force on the proximal phalange perpendicular the long-axis thereof;
said rod assembly continuously adjustable in length, whereby a continuously adjustable static flexion force may be applied to the phalange/metacarpal joint.

22. The device in claim 21 in which said support means includes edge means defining a plurality of openings therein, said openings spaced various distances from said base and said first end of said rod assembly rotatably attached to said support member by a portion of said rod extending through one of said openings in said support member.

23. A passive flexion device for a finger comprising:
a base adapted for attachment to the hand adjacent the palm;
a support member extending from said base and attached thereto by attaching means;
a rod assembly having a first end attached to said support member and a second end adapted for attachment to the proximal phalanx;
said rod extending from said support member in an manner to produce a flexion force on the proximal phalange perpendicular the long-axis thereof;
said rod assembly continuously adjustable in length, said rod assembly including a first sleeve member attached to said support member and a second sleeve member telescopingly threadably joined with said first sleeve member, whereby rotation of said first sleeve member will cause said members to telescope and a continuously adjustable static flexion force may be applied to the phalange/metacarpal joint.

24. The device in claim 23 in which said rod assembly further includes a third sleeve member telescopingly threadably joined with said second sleeve member, whereby rotation of said first sleeve will cause said second and third sleeve members to telescope when said first and second sleeve members are fully telescoped and rotating together.

25. The device in claim 24 in which said rod assembly further includes a fourth sleeve member telescopingly threadably joined with said third sleeve member and including a hook portion on an end opposite the portion joined with said third sleeve member, whereby rotation of said first sleeve will cause said third and fourth sleeve members to telescope when said second and third sleeve members are fully telescoped and rotating together.

26. A passive flexion device adapted to be attached adjacent the palm of a hand by a strap extending around the hand for applying passive flexion to a finger on the hand, said device comprising:
a base configured to substantially conform to the palm of the hand, said base including means defining a lateral passage through said base configured to receive a strap through said passage;
a support member extending from said base and attached thereto by attaching means;
a rod assembly having a first end attached to said support member and a second end adapted for attachment to the proximal phalanx;
said rod extending from said support member in a manner to produce a flexion force on the proximal phalange perpendicular the long-axis thereof;
said rod assembly continuously manually adjustable in length, whereby a continuously adjustable static flexion force may be applied to the phalange/metacarpal joint, said base including a bottom plate conforming to the palm of the hand and a second upper plate spaced from said first plate, said passage being defined between said plates; and
traction means for applying a traction force along the long-axis of the finger and pivot means for pivotally attaching said traction means to said second plate.

27. The device in claim 26 in which said traction means includes an elongated shaft extending from said base, and pulling means associated with an end of said shaft opposite said pivot means for applying a force parallel said shaft and away from said base.

28. The device in claim 27 in which said pulling means includes a pulley on said end of said shaft, a line extending over said pulley and tensioning means for attaching one end of said line selectively to a position along said shaft.

29. The device in claim 28 in which said line includes a tension spring portion.

* * * * *

UNITED STATES PATENT AND TRADEMARK OFFICE
CERTIFICATE OF CORRECTION

PATENT NO. : 4,945,902

DATED : August 7, 1990

INVENTOR(S) : Robert E. Dorer and Lawrence Belden

It is certified that error appears in the above-identified patent and that said Letters Patent is hereby corrected as shown below:

Column 2, Line 27:

After "by" insert --VELCRO$^{TM}$--

Column 3, Line 11:

After "assembly" insert --.--

Column 4, Line 37:

"1B"" should be --18"--

Column 5, Line 6:

"45-90" should be --45-90°--

Column 5, Line 28:

After "further" insert --.--

Column 6, Claim 2, Line 13:

"first and" should be --first end--

Column 7, Claim 14, Line 62:

"en gaging" should be --engaging--

UNITED STATES PATENT AND TRADEMARK OFFICE
CERTIFICATE OF CORRECTION

PATENT NO. : 4,945,902
DATED : August 7, 1990
INVENTOR(S) : Robert E. Dorer and Lawrence Belden It is certified that error appears in the above-identified patent and that said Letters Patent is hereby corrected as shown below:

Column 8, Claim 19, Line 22:

After "thereto" insert --by--

Column 9, Claim 23, Line 18:

"in an" should be --in a--

Signed and Sealed this

Fourteenth Day of May, 1991

Attest:

HARRY F. MANBECK, JR.

*Attesting Officer*         *Commissioner of Patents and Trademarks*